(12) United States Patent
Schiff et al.

(10) Patent No.: US 10,960,139 B2
(45) Date of Patent: Mar. 30, 2021

(54) SYRINGE ASSEMBLY HAVING A ROTATABLY ADVANCEABLE PLUNGER ROD

(71) Applicant: Becton Dickinson France, S.A.S., Le Pont-de-Claix (FR)

(72) Inventors: David Robert Schiff, Highland Park, NJ (US); Mathieu Dominic Turpault, Pennington, NJ (US); Antonio Gatta, Philadelphia, PA (US); John Depler Coleman, Philadelphia, PA (US)

(73) Assignee: Becton Dickinson France, S.A.S., Le Pont-de-Claix (FR)

( * ) Notice: Subject to any disclaimer, the term of this patent is extended or adjusted under 35 U.S.C. 154(b) by 64 days.

(21) Appl. No.: 16/217,488

(22) Filed: Dec. 12, 2018

(65) Prior Publication Data

US 2019/0111212 A1     Apr. 18, 2019

Related U.S. Application Data

(63) Continuation of application No. 13/622,378, filed on Sep. 19, 2012, now abandoned.

(Continued)

(51) Int. Cl.
*A61M 5/315*     (2006.01)
*A61M 5/31*      (2006.01)

(52) U.S. Cl.
CPC . *A61M 5/31511* (2013.01); *A61M 2005/3118* (2013.01); *A61M 2005/3121* (2013.01); *A61M 2005/31518* (2013.01)

(58) Field of Classification Search
CPC .......... A61M 5/31515; A61M 5/31528; A61M 5/31535; A61M 5/31551; A61M 5/31553;
(Continued)

(56) References Cited

U.S. PATENT DOCUMENTS 4,923,446 A * 5/1990 Page .................. A61M 5/3243
604/198
2003/0045838 A1   3/2003 Woodard, Jr. et al.
(Continued)

FOREIGN PATENT DOCUMENTS

DE     3833138 A1    4/1990
WO    03020341 A2    3/2003
(Continued)

*Primary Examiner* — Manuel A Mendez
*Assistant Examiner* — Justin L Zamory
(74) *Attorney, Agent, or Firm* — The Webb Law Firm (57) ABSTRACT

A syringe assembly for use as a pre-filled syringe is disclosed. The syringe assembly includes a syringe barrel defining a chamber and having a stopper disposed therein. A plunger rod includes an inner member engaged with a portion of the stopper and an outer member adapted for rotational advancement with respect to the inner member to axially displace the outer member with respect to the inner member. The plunger rod is transitionable from a collapsed position in which a portion of the inner member is nested within the outer member, to an extended position in which the same portion of the inner member extends outside the outer member. The inner member includes a radial extension and the outer member defines a helical track adapted to receive the radial extension therein.

18 Claims, 6 Drawing Sheets

Related U.S. Application Data (60) Provisional application No. 61/541,370, filed on Sep. 30, 2011.

(58) Field of Classification Search
CPC ...... A61M 5/31555; A61M 2005/2073; A61M 2005/2093; A61M 5/3158–31586; A61M 5/31511; A61M 5/3155; A61M 5/3272
See application file for complete search history.

(56) References Cited

U.S. PATENT DOCUMENTS

| | | |
|---|---|---|
| 2005/0033244 A1 | 2/2005 | Veasey et al. |
| 2006/0247581 A1 | 11/2006 | Pedersen et al. |
| 2009/0318880 A1* | 12/2009 | Janish ............... A61M 5/31511 604/228 |
| 2010/0228200 A1 | 9/2010 | Moed |
| 2012/0041366 A1 | 2/2012 | Fayyaz et al. |

FOREIGN PATENT DOCUMENTS

| | | |
|---|---|---|
| WO | 03037411 A1 | 5/2003 |
| WO | 2006136769 A1 | 12/2006 |
| WO | 2010033778 A2 | 3/2010 |

\* cited by examiner

SYRINGE ASSEMBLY HAVING A ROTATABLY ADVANCEABLE PLUNGER ROD

CROSS-REFERENCE TO RELATED APPLICATION

This application is a continuation of U.S. patent application Ser. No. 13/622,378 filed Sep. 19, 2012, which claims priority to U.S. Provisional Patent Application No. 61/541,370 filed Sep. 30, 2011, the entire disclosures of each of which are hereby incorporated by reference.

BACKGROUND OF THE INVENTION

Field of the Invention

The present invention is directed to a pre-filled syringe assembly adapted for the dispensing and delivery of a fluid. More particularly, the present invention is directed to a pre-filled syringe assembly having a rotatably advanceable plunger rod which results in a smaller packaging footprint allowing for reduced storage space.

Description of Related Art

Syringe assemblies, and in particular hypodermic syringes, are well known in the medical field for dispensing fluids, such as medication. A conventional syringe typically includes a syringe barrel with an opening at one end and a plunger mechanism disposed through the other end. The plunger mechanism typically includes a plunger rod extending through the barrel, with a plunger head or stopper at the end of the plunger rod within the barrel and with a finger flange at the other end of the plunger rod extending out of the barrel. In use, the plunger rod is retracted through the syringe barrel to fill the syringe barrel with a fluid, such as a medication, with the plunger rod extending out from the rear end of the syringe barrel. For delivery of the medication to a patient, the opening of the syringe barrel is adapted for fluid communication with a patient, such as through a hypodermic needle fitted at the front end of the syringe barrel or through a luer-type fitting extending from the front end of the syringe barrel for attachment with a fluid line of a patient. Upon depression of the plunger rod, the plunger rod and stopper travel through the syringe barrel, thereby forcing the contents of the syringe out through the opening at the front end for delivery to the patient. Such an operation is well known in the medical field, and medical practitioners have become well accustomed to the use of such common fluid delivery procedures through standard syringes.

Conventional syringes are well known to be used in connection with a vial of a medication, where the user draws the fluid into the syringe immediately prior to injection and delivery of the fluid to the patient. Oftentimes, hypodermic syringes may be packaged as "pre-filled" devices, wherein the syringe is pre-filled with medication prior to being packaged and delivered to the end user. In this manner, there is no need for the user to fill the device prior to injection, thereby saving time for the end user and maintaining consistent volumes for delivery.

Pre-filled syringes and pre-filled metered dose syringes are often filled with narcotics or other drugs at a production facility, packaged, and then shipped to a medical facility. Once at the facility, these syringes are often placed in controlled storage and/or locked cabinets to reduce theft of the syringes themselves and/or theft of the contents of these syringes. The space within these controlled storage locations is often limited, thus there is a need for a syringe assembly that has a smaller packaging footprint to reduce the storage space required for containing this syringe. It is also desirable to produce syringes that are uniform in terms of an outer surface shape to allow for stacking of the syringes within the storage cabinet. There is a further need for syringe assemblies having a smaller packaging footprint that include tamper-evident indicators to allow medical practitioners to determine whether the contents of a syringe assembly have been compromised.

SUMMARY OF THE INVENTION

In accordance with an embodiment of the present invention, a syringe assembly includes a syringe barrel having a first end, a second end, and a sidewall extending therebetween defining a chamber. A stopper is slideably disposed at least partially within the chamber. A plunger rod for advancing the stopper includes an inner member engaged with a portion of the stopper and an outer member adapted for rotational advancement with respect to the inner member to axially displace the outer member with respect to the inner member. The plunger rod is transitionable from a collapsed position in which a portion of the inner member is nested within the outer member, to an extended position in which the same portion of the inner member extends outside the outer member.

In certain configurations, the inner member includes a radial extension and the outer member defines a track adapted to receive the radial extension therein. The track may be at least partially helical about an outer surface of the outer member. The radial extension may remain substantially stationary during transition of the plunger rod from the collapsed position to the extended position, and the outer member may be rotated about the inner member to axially displace the outer member with respect to the inner member. In certain configurations, the track extends between a proximal end and a distal end, with the distal end including a restraint for locking the radial extension therein in the extended position. The stopper may remain substantially stationary during transition of the plunger rod from the collapsed position to the extended position. The syringe assembly may also include a medication or drug disposed within the chamber.

In accordance with another embodiment of the present invention, a plunger rod assembly for use with a syringe assembly includes an inner member having a distal end configured for securement to a stopper disposed within a syringe barrel. The plunger rod assembly also includes an outer member having an open portion configured for rotational advancement with respect to the inner member to axially displace the outer member with respect to the inner member. The plunger rod assembly is transitionable from a collapsed position in which a portion of the inner member is nested within the outer member, to an extended position in which the same portion of the inner member extends outside the outer member. The plunger rod assembly also includes a restraint configured to limit axial advancement of the outer member with respect to the inner member in the extended position.

The restraint may be configured to limit axial advancement of the outer member in both the proximal direction and the distal direction in the extended position. The inner member may include a radial extension and the outer member may define a track adapted to receive the radial extension therein. The track may be at least partially helical about an outer surface of the outer member. In certain configurations, the radial extension remains substantially stationary during transition of the plunger rod assembly from the collapsed position to the extended position. In other configurations, the track may extend between a proximal end and a distal end, with the distal end including a restraint for locking the radial extension therein in the extended position.

In accordance with yet another embodiment of the present invention, a syringe assembly includes a syringe barrel having a first end, a second end, and a sidewall extending therebetween defining a chamber. The syringe assembly also includes a stopper slideably disposed at least partially within the chamber, and a plunger rod. The plunger rod includes an inner member engaged with a portion of the stopper and includes a radial extension, and an outer member defining a track adapted to receive the radial extension therein. Rotation of the outer member about the inner member axially displaces the track about the radial extension to transition the plunger rod from a collapsed position in which a portion of the inner member is nested within the outer member, to an extended position in which the same portion of the inner member extends outside the outer member.

In certain configurations, the track is at least partially helical about an outer surface of the outer member. In other configurations, an initial portion of the inner member and an initial portion of the outer member are disposed within the syringe barrel in the collapsed position. The initial portion of the outer member may, however, be external to the syringe barrel in the extended position. Optionally, the track extends between a proximal end and a distal end, with the distal end including a restraint for locking the radial extension therein in the extended position. In a further configuration, a medication or a drug is disposed within the chamber of the syringe barrel.

DETAILED DESCRIPTION OF THE EMBODIMENTS

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Figure 7:
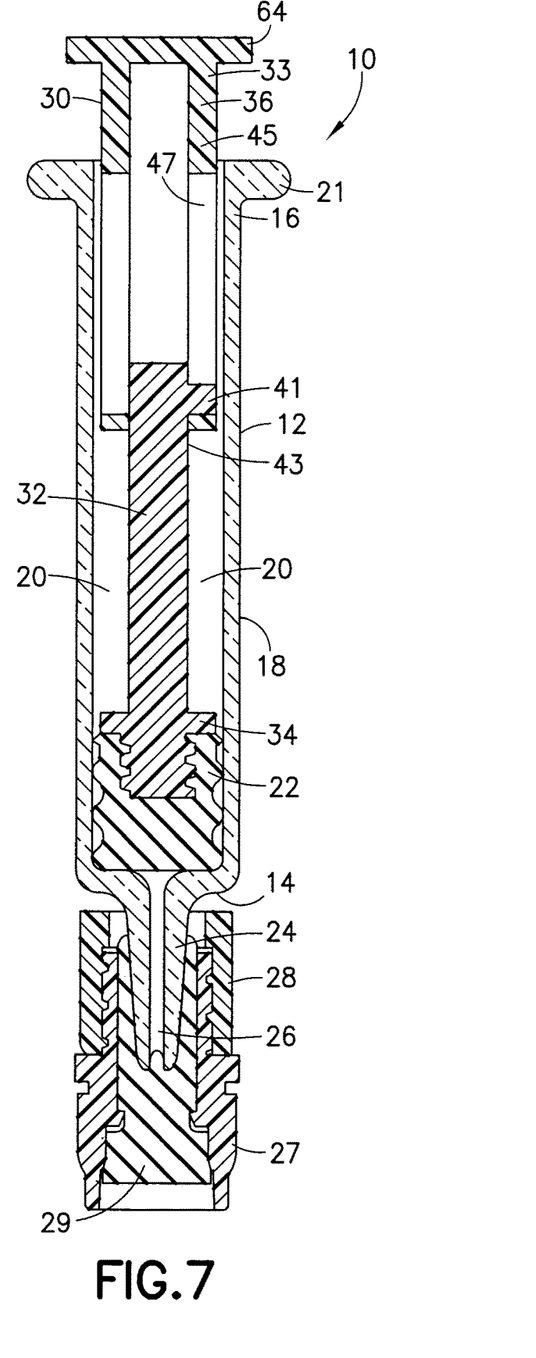
FIG. 7 is a cross-sectional view of the syringe assembly of FIG. 1 taken along line 7-7 of FIG. 6 in accordance with an embodiment of the present invention.
Figure 8:
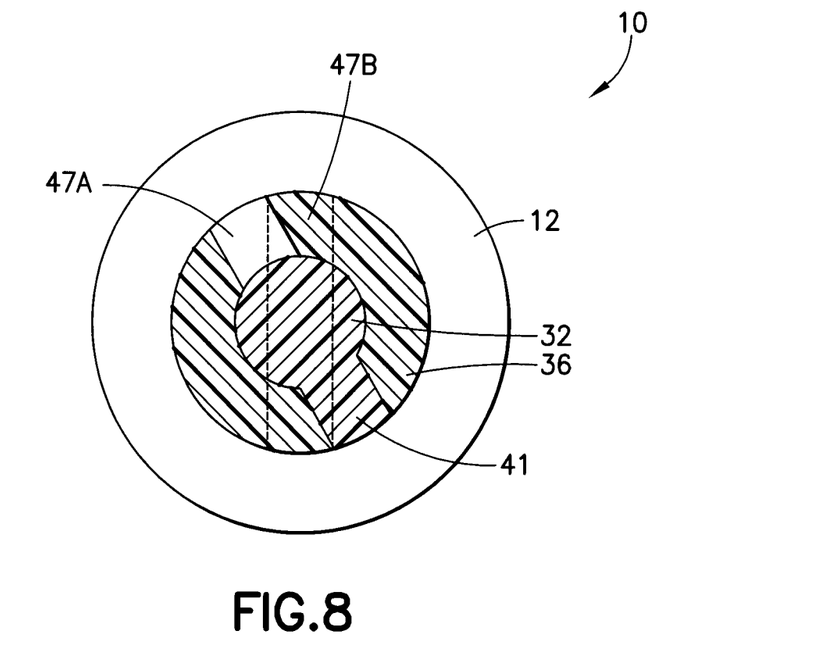
FIG. 8 is a cross-sectional view of the syringe assembly of FIG. 1 taken along line 8-8 of FIG. 3 in accordance with an embodiment of the present invention.
Figure 9:
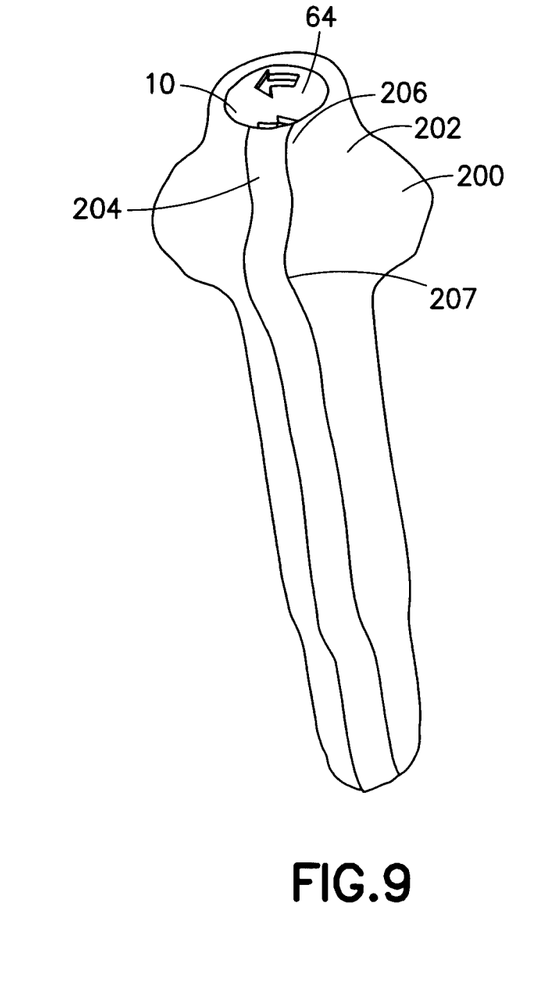
FIG. 9 is a perspective view of the syringe assembly of FIG. 1 including a tamper-evident packaging disposed thereover in accordance with an embodiment of the present invention.
Figure 10:
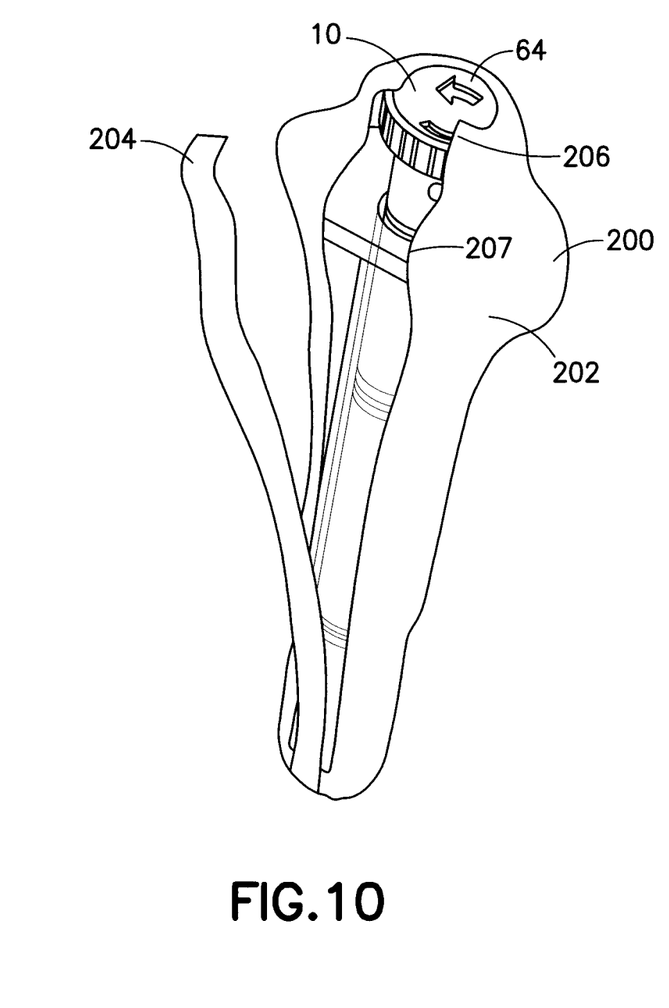
FIG. 10 is a perspective view of the syringe assembly of FIG. 9 having the tamper-evident packaging partially removed therefrom in accordance with an embodiment of the present invention.

Reference is now made to FIGS. 1-8, which depict a syringe assembly according to an embodiment of the present invention, generally indicated as 10, adapted for the dispensing and delivery of a fluid. FIGS. 9-10 depict a packaging assembly, generally indicated as 200, and the operational steps for removing the packaging assembly, which can be used for packaging the syringe assembly of the invention.

With particular reference to FIGS. 1-8, the syringe assembly 10 is intended for use for injection or infusion of fluid, such as a medication, directly into a patient, and is generally shown and described for purposes of the present description as a hypodermic syringe. Syringe assembly 10 is contemplated for use in connection with a needle such as by connecting syringe assembly 10 to a separate needle assembly (not shown), or alternatively for connection with a separate intravenous (IV) connection assembly (not shown).

The syringe assembly 10 includes a syringe barrel 12 having a first or distal end 14, a second or proximal end 16, and a sidewall 18 extending between the distal end 14 and proximal end 16 defining an interior chamber 20 of the syringe barrel 12. A stopper 22 is slidably disposed within the chamber 20 of the syringe barrel 12. The syringe barrel 12 may be in the general form of an elongated cylindrical barrel as is known in the art for the general shape of a hypodermic syringe, although other forms for containing a fluid for delivery are also contemplated by the present invention. Additionally, the syringe barrel 12 may be formed of glass, or may be injection molded from thermoplastic material such as polypropylene and polyethylene according to techniques known to those of ordinary skill in the art, though it is to be appreciated that the syringe barrel 12 may be made from other suitable materials and according to other applicable techniques. In certain configurations, the syringe barrel 12 may include an outwardly extending flange 21 about at least a portion of the proximal end 16. The flange 21 may be configured for easy grasping by a medical practitioner, as will be discussed herein.

Figure 3:
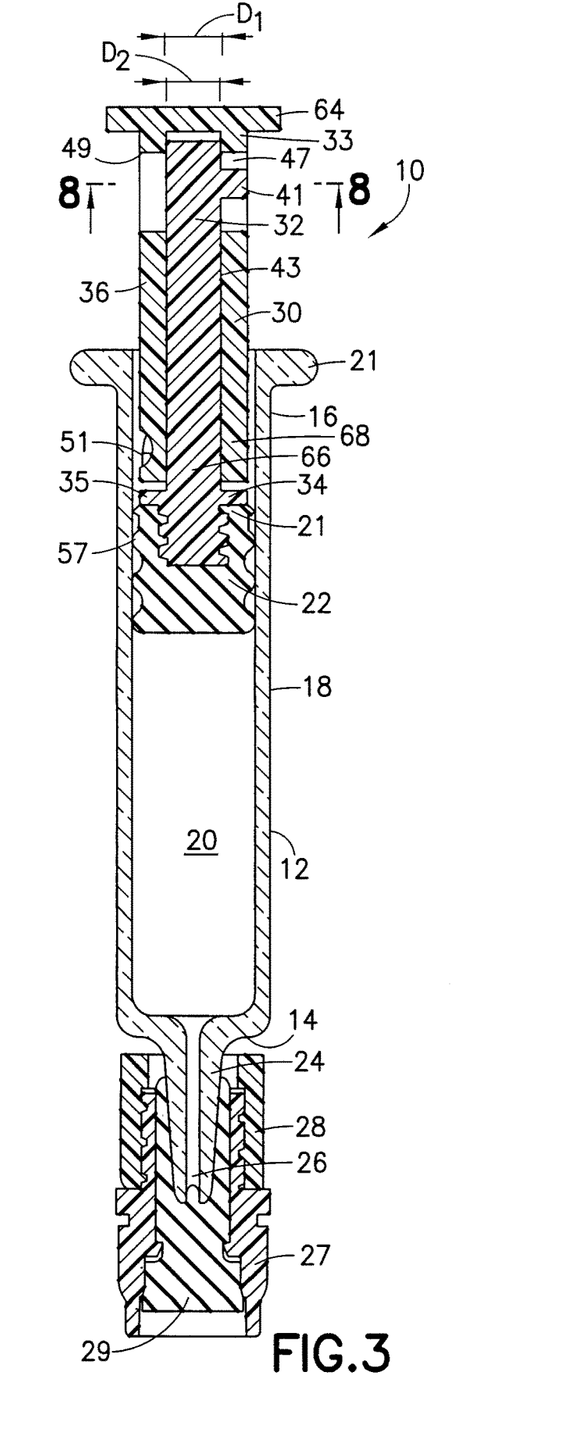
FIG. 3 is a cross-sectional view of the syringe assembly of FIG. 1 taken along line 3-3 of FIG. 2 in accordance with an embodiment of the present invention.

As illustrated in FIG. 3, the distal end 14 of the syringe barrel 12 terminates in a tip 24 having an outlet opening 26. The proximal end 16 is generally open-ended, but is intended to be closed off to the external environment, via the stopper 22, as will be discussed herein. According to one non-limiting embodiment, as shown in FIG. 3, the syringe assembly 10 can include a tip cap 28, an interface member 27 interfacing between the tip cap 28 and the tip 24 of the syringe barrel 12, and a plug 29, for sealing the outlet opening 26.

The syringe barrel 12 may include markings, such as graduations on the sidewall 18 thereof, for providing an indication as to the level or amount of fluid contained within the syringe barrel 12. Such markings may be provided on the external wall, the internal wall, or integrally formed or otherwise within the wall of syringe barrel 12. Alternatively, or in addition thereto, the markings may provide a description of the contents of the syringe, or other identifying information, as may be known in the art.

As noted, distal end 14 of syringe barrel 12 includes an outlet opening 26. The profile of outlet opening 26 may be adapted for engagement with a separate dispensing device, such as a needle assembly or IV connection assembly, and therefore may include a mechanism for such engagement, for example, a generally tapered luer tip, for engagement with a separate tapered luer mating surface (not shown) of such a separate device for attachment therewith. In addition, a mechanism for locking engagement therebetween may also be provided, such as a luer collar or luer lock including interior threads. Such luer connections and luer locking mechanisms are well known in the art.

All of the components of syringe assembly 10 may be constructed of any known material, and are desirably constructed of medical grade polymers. As stated above, the syringe assembly 10 is particularly useful as a pre-filled syringe, and therefore may be provided for end use with a fluid, such as a medication, contained within interior chamber 20 of syringe barrel 12, pre-filled by the manufacturer. In this manner, syringe assembly 10 can be manufactured, pre-filled with a medication, sterilized, and packaged in appropriate packaging for delivery, storage, and use by the end user, without the need for the end user to fill the syringe with medication from a separate vial prior to use.

With continuing reference to FIGS. 1-8, the syringe assembly 10 includes a plunger rod assembly, generally indicated as 30, for controlling movement of the stopper 22 slideably through the syringe barrel 12 to either expel the syringe contents of a pre-filled type of syringe assembly 10 or, depending upon the desired use of the syringe assembly, to aspirate or withdraw a fluid into the syringe barrel 12. The plunger rod assembly 30 includes an inner member 32, as shown clearly in FIG. 3, including a distal end 34 secured to the stopper 22. In one embodiment, the distal end 34 of the inner member 32 may be secured to the stopper 22 by way of a threaded engagement formed therebetween. In another embodiment, the distal end 34 of the inner member 32 may be co-formed with the stopper 22, such as by a two-shot molding process. In still a further embodiment, the distal end 34 of the inner member 32 may include an engagement plate 35 for receiving a portion of the stopper 22, such as the flange 21 of the stopper 22, therewith. The inner member 32 may be substantially cylindrical, although it is contemplated herein that other shapes may also be included in the present invention.

In one configuration, the inner member 32 includes a radial extension 41 extending radially outward from a portion of a sidewall 43 thereof. The radial extension 41 may include a protrusion or other extension extending outwardly from the sidewall 43.

The plunger rod assembly 30 also includes an outer member 36 which is adapted for rotational advancement with respect to the inner member 32. The outer member 36 may also be substantially cylindrical and may include a hollow core 39, as shown in FIG. 5, although it is contemplated herein that other shapes corresponding to the shape of the inner member 32 may also be included in the present invention. A sidewall 45 of the outer member 36 may include a track 47 disposed therein extending from the external environment into the hollow core 39. In one configuration, the track extends within the sidewall 45 of the outer member 36 from a proximal end 49 of the outer member 36 to a distal end 51 of the outer member 36, as shown clearly in FIG. 4. In a further configuration, the track is at least partially helically disposed within the sidewall 45 about an outer surface circumference of the outer member 36. The track 47 is dimensioned to receive the radial extension 41 of the inner member 32 therein.

The plunger rod assembly 30 can include a thumb press portion 64 or any other type of well-known member, upon which a user can apply a distally directed force to cause the plunger rod 30 to move the stopper 22, disposed within the syringe barrel 12, toward the distal end 14 of the syringe barrel 12 to expel the syringe contents during operation of the syringe assembly 10. This thumb press portion 64 can include a roughened or serrated surface, as is known in the art, to provide a frictional surface for assisting the user in movement or actuation of the plunger rod. In one embodiment, the thumb press portion 64 may be disposed adjacent a proximal end 33 of the outer member 36.

Figure 1:
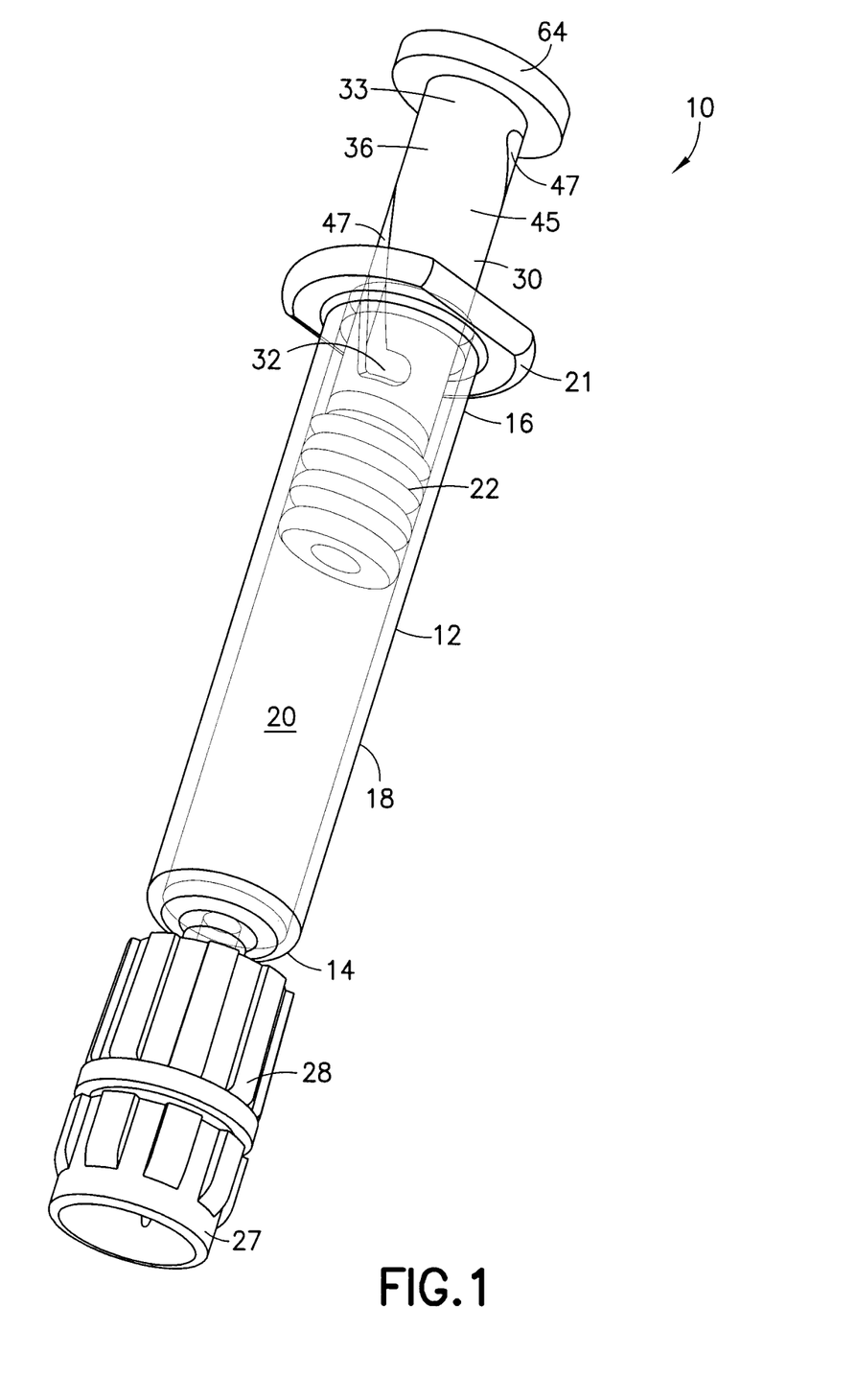
FIG. 1 is a perspective view of a syringe assembly including a rotatably advanceable plunger rod in an initial collapsed position in accordance with an embodiment of the present invention.
Figure 2:
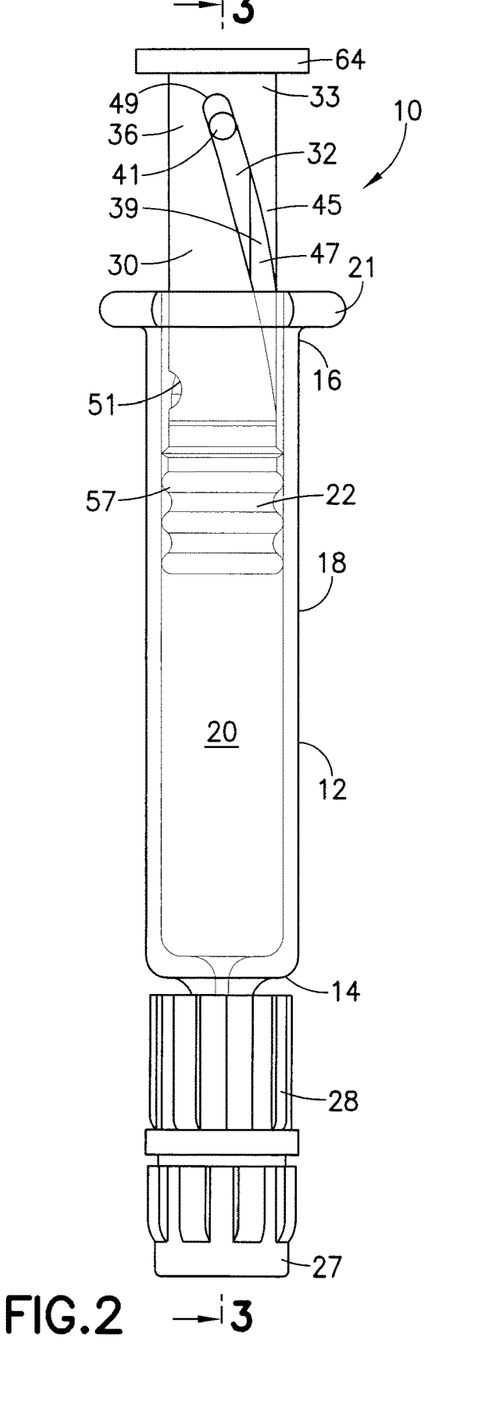
FIG. 2 is a front view of the syringe assembly of FIG. 1 showing a locking tab of the plunger rod in a first position in the initial collapsed position in accordance with an embodiment of the present invention.
Figure 4:
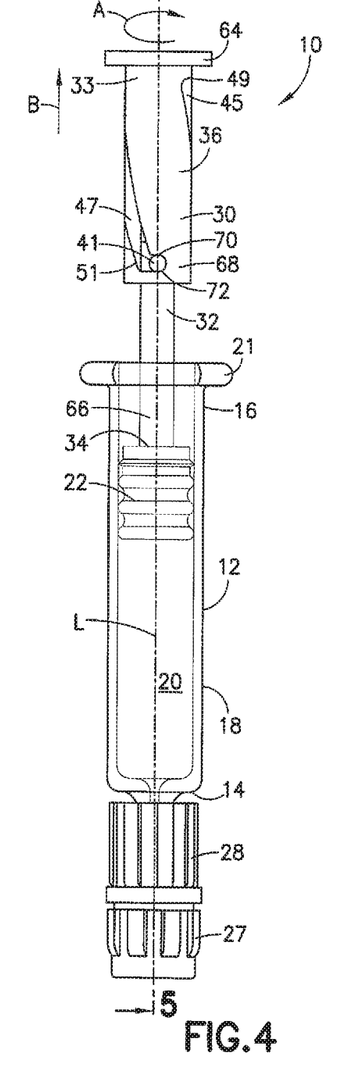
FIG. 4 is a front view of the syringe assembly of FIG. 1 showing the locking tab of the plunger rod in the extended ready-to-use position in accordance with an embodiment of the present invention.
Figure 5:
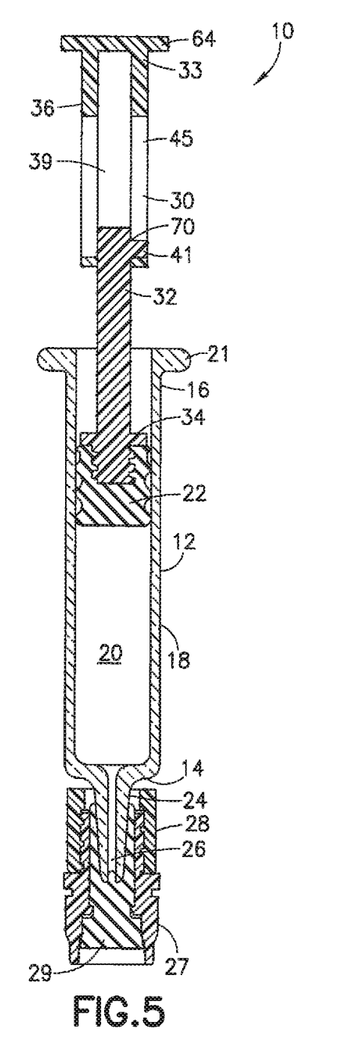
FIG. 5 is a cross-sectional view of the syringe assembly of FIG. 1 taken along line 5-5 of FIG. 4 in accordance with an embodiment of the present invention.
Figure 6:
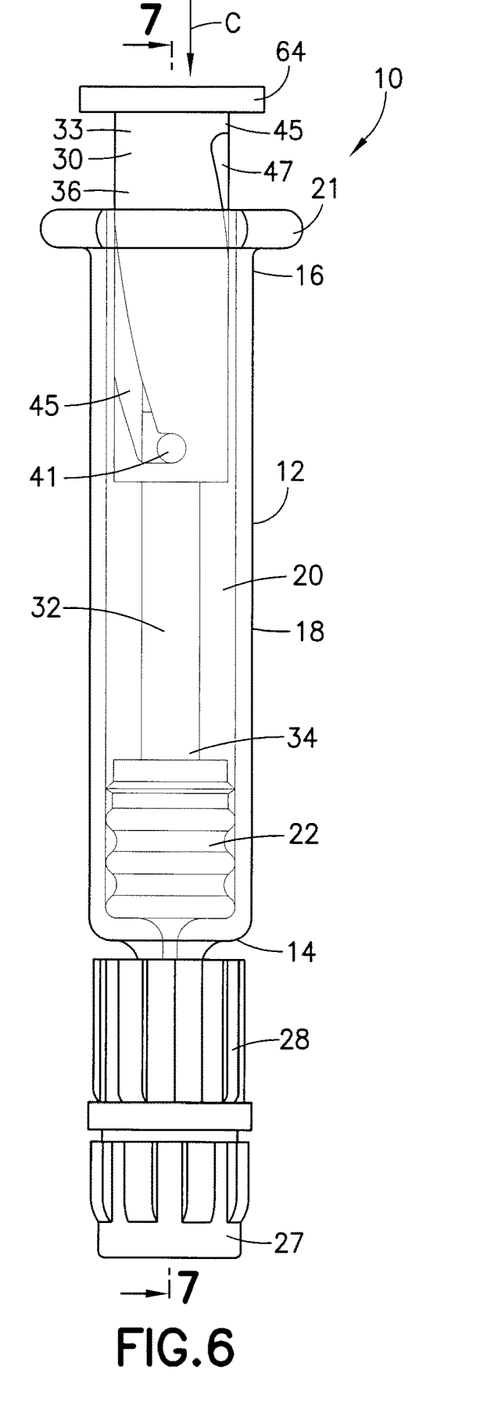
FIG. 6 is a front view of the syringe assembly of FIG. 1 showing the locking tab of the plunger rod in the extended ready-to-use position and the plunger rod deployed within the syringe barrel in accordance with an embodiment of the present invention.

The plunger rod assembly 30 is transitionable from a collapsed pre-use position, as shown in FIGS. 1-3, to an extended ready-to-use position, as shown in FIGS. 4-5, to a used position, as shown in FIGS. 6-7.

In the collapsed pre-use position, as shown in FIGS. 1-3, at least a portion of the inner member 32 is nested within a portion of the outer member 36. In this configuration, at least a portion of the outer member 36 includes an inner diameter $D_1$, as shown in FIG. 3, that is greater than the external diameter $D_2$ of at least a portion of the inner member 32. Accordingly, outer member 36 is adapted to encompass at least a portion of inner member 32 in the collapsed pre-use position, such that the inner member 32 is nested within the outer member 36. In the collapsed position, the stopper 22 may be disposed within the chamber 20 at a substantially proximal location 57, and the inner member 32 connected thereto may extend outwardly of the syringe barrel 12 within the hollow core 39 of the outer member 36. The radial extension 41 of the inner member 32 is disposed within the track 47 of the outer member 36 at a first location adjacent the proximal end 49 of the outer member 36.

In order to transition the plunger rod assembly 30 from the collapsed pre-use position to the extended ready-to-use position, a medical practitioner may rotate the outer member 36 about the inner member 32, such as by twisting the outer member 36 in the direction shown by arrow A of FIG. 4. The medical practitioner may grasp any portion of the outer member 36, such as the thumb press 64, to effectuate this rotation. Rotation of the outer member 36 with respect to the inner member 32 causes the outer member 36 to be axially displaced from the inner member 32 along a longitudinal axis L, as shown in FIG. 4, of the syringe assembly 10 from a distal orientation, as shown in FIGS. 1-3, to a proximal location, as shown in FIGS. 4-5. Once the plunger rod assembly 30 is transitioned from the collapsed pre-use position to the extended ready-to-use position, at least a portion of the inner member 32 that was nested within the outer member 36 in the collapsed position, extends outside the outer member 36 in the extended position.

In one configuration, the inner member 32 is disposed in substantially the same position during the transition from the collapsed position to the extended position. Specifically, the radial extension 41 of the inner member 32 may be disposed in substantially the same position during the transition from the collapsed position to the extended position. In a further configuration, the stopper 22 remains substantially stationary within the chamber 20 of the syringe barrel 12 during transition of the plunger rod assembly 30 from the collapsed position to the extended position. In a further configuration, an initial portion 66 of the inner member 32 and an initial portion 68 of the outer member 36 are disposed within a portion of the syringe barrel 12, as shown in FIG. 3, in the collapsed position. In the extended position, the initial portion 66 of the inner member 32 may remain disposed within a portion of the syringe barrel 12, however, the initial portion 68 of the outer member 36 is disposed external to the syringe barrel 12.

As shown specifically in FIG. 4, the track 47 adjacent the distal end 51 of the outer member 36 may include a restraint 70 for locking the radial extension 41 therein in the extended position. In one configuration, the restraint 70 may include a flattened recess 72 such that the radial extension 41 is secured within the recess 72 to prevent further axial movement of the outer member 36 with respect to the inner member 32. In one configuration, the restraint 70 is configured to limit further axial movement of the outer member 36 with respect to the inner member 32 in the proximal direction once the plunger rod assembly 30 has been transitioned to the extended position. Accordingly, the application of force in the direction of arrow B, as shown in FIG. 4, does not allow for further displacement of the outer member 36 with respect to the inner member 32 once the plunger rod assembly 30 has been transitioned to the extended position. In still a further configuration, the restraint 70, shown in FIGS. 4-5, also limits relative movement between the outer member 36 and the inner member 32 in the direction shown by arrow C of FIG. 6. Accordingly, once the plunger rod assembly 30 has been transitioned to the extended position, as shown in FIGS. 4-5, application of a downward force in the direction of arrow C allows the locked outer member 36 and inner member 32 to advance the stopper 22 within the chamber 20, and does not allow for relative movement between the outer member 36 and the inner member 32. FIG. 8 illustrates a portion of the track 47A adjacent the proximal end 49 of the outer member 36 for receiving the radial extension 41 in the collapsed position, and a portion of the track 47B adjacent the distal end 51 of the outer member 36 receiving the radial extension 41 therein in the extended position.

With the plunger rod assembly 30 locked in position such that the outer member 36 and the inner member 32 move together, the syringe assembly 10 may be transitioned to the used position, as shown in FIGS. 6-7. During transition of the plunger rod assembly 30 from the extended position to the used position, a medication or drug disposed within the chamber 20 may be expelled therefrom by the advancement of the stopper 22, as is conventionally known.

It is noted herein that the radial extension 41 may extend outwardly from the inner member 32 into a portion of the outer member 36 in any suitable dimension that allows the combined plunger assembly 30 to be deployed into the interior of the syringe barrel 12 without obstruction.

Reference is now made to FIGS. 9-10, which depict a packaging assembly, generally indicated as 200, and the sequential operational steps for removing the packaging assembly 200 from the syringe assembly 10, in accordance with an embodiment of the present invention. The packaging assembly 200 includes a molded cover 202 configured for placement about a portion of the syringe barrel 12, the plunger rod assembly 30, and the tip cap 28. A tear tab 204 can be associated with one end 206 of the molded cover 202. The tear tab 204 is configured, such as by the inclusion of a frangible portion 207, to facilitate removal of the molded cover 202 from the syringe assembly 10, and can be positioned adjacent a top surface or thumb press 64 of the plunger rod assembly 30. The tear tab 204 can include a roughened or serrated surface, as is known in the art, to provide a frictional surface for assisting the user in grasping of the tear tab 204. The cover 202 is configured for placement about the syringe assembly 10 to constrain the plunger rod assembly 30 from inadvertent transition from the collapsed position to the extended position and to prevent tampering of the syringe assembly 10.

It can be appreciated that each of the syringe assemblies of the present invention includes a reduced footprint which is desirable in the packaging of the syringe assemblies as it requires less packaging. This reduced footprint provides for syringe assemblies having consistently sized profiles which allow for easy stacking and require less storage space, both of these features being desirable in a controlled storage environment.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of invention.

What is claimed is:

1. A syringe assembly, comprising:
a syringe barrel having a first end, an open second end, and a sidewall extending therebetween defining a chamber;
a stopper slideably disposed at least partially within the chamber; and
a plunger rod extending from the stopper through the open second end of the syringe barrel, the plunger rod comprising an inner member engaged with a portion of the stopper and an outer member adapted for rotational advancement with respect to the inner member to axially displace the outer member with respect to the inner member,
wherein the plunger rod is configured such that, while a distal portion of the plunger rod and the stopper are disposed in the syringe barrel, twisting at least a portion of the outer member about the inner member without grasping the inner member causes the outer member of the plunger rod to move proximally away from the open second end of the syringe barrel thereby transitioning the plunger rod from a collapsed position, in which a portion of the inner member is nested within the outer member, to an extended position, in which the same portion of the inner member extends outside the outer member,
wherein the inner member comprises a non-helical radial extension and the outer member defines a track adapted to receive the radial extension therein, and
wherein the track extends within a sidewall of the outer member between a proximal end and a distal end thereof, the track comprising a helical portion, which defines a helical path for the non-helical radial extension, and a circumferential portion, which defines a path for the radial extension about a portion of the circumference of the outer member, at the distal end of the track, the circumferential portion forming a restraint for locking the radial extension therein in the extended position.

2. The syringe assembly of claim 1, wherein the plunger rod is configured to be transitioned from the collapsed position to the extended position by grasping and twisting the outer member with one hand.

3. The syringe assembly of claim 1, wherein the plunger rod transitions from the collapsed position to the extended position by twisting the outer member a complete rotation about the inner member.

4. The syringe assembly of claim 1, wherein when the radial extension is in the circumferential portion of the track, the radial extension prevents axial movement of the outer member with respect to the inner member.

5. The syringe assembly of claim 1, wherein the radial extension remains substantially stationary during transition of the plunger rod from the collapsed position to the extended position.

6. The syringe assembly of claim 1, further comprising a medication or drug disposed within the chamber.

7. The syringe assembly of claim 1, wherein, when the plunger rod is in the collapsed position, twisting the outer member relative to the inner member in a first direction causes the radial extension to initially pass through the helical portion of the track, and wherein continued twisting of the outer member relative to the inner member in the first direction moves the radial extension into the circumferential portion of the track.

8. The syringe assembly of claim 7, wherein a length of the helical portion of the track is greater than a length of the circumferential portion of the track.

9. The syringe assembly of claim 1, wherein the non-helical radial extension comprises a rigid protrusion.

10. A plunger rod assembly comprising a plunger rod for use with a syringe assembly, the plunger rod comprising:
   an inner member having a distal end configured for securement to a stopper disposed within a syringe barrel;
   an outer member having an open portion configured for rotational advancement with respect to the inner member to axially displace the outer member with respect to the inner member; and
   a restraint configured to limit axial advancement of the outer member with respect to the inner member,
   wherein the inner member comprises a non-helical radial extension and the outer member defines a track adapted to receive the radial extension therein,
   wherein the plunger rod is configured such that, while the distal end of the plunger rod and stopper are disposed in the syringe barrel, twisting at least a portion of the outer member about to the inner member without grasping the inner member causes the outer member of the plunger rod to move proximally away from the open second end of the syringe barrel thereby transitioning the plunger rod from a collapsed position, in which a portion of the inner member is nested within the outer member, to an extended position, in which the portion of the inner member extends outside the outer member, and
   wherein the track extends within a sidewall of the outer member between a proximal end and a distal end thereof, the track comprising a helical portion, which defines a helical path for the non-helical radial extension, and a circumferential portion, which defines a path for the radial extension about a portion of the circumference of the outer member, at the distal end of the track, the circumferential portion forming the restraint, which locks the radial extension therein in the extended position.

11. The plunger rod assembly of claim 10, wherein the plunger rod is configured to be transitioned from the collapsed position to the extended position by grasping and twisting the outer member with one hand.

12. The plunger rod assembly of claim 10, wherein the plunger rod transitions from the collapsed position to the extended position by twisting the outer member a complete rotation about the inner member.

13. The plunger rod assembly of claim 10, wherein with the radial extension in the circumferential portion of the track, the radial extension prevents axial movement of the outer member with respect to the inner member.

14. The plunger rod assembly of claim 10, wherein when the radial extension is in the circumferential portion of the track, the radial extension limits axial advancement of the outer member in both a proximal direction and a distal direction.

15. The plunger rod assembly of claim 10, wherein the radial extension remains substantially stationary during transition of the plunger rod from the collapsed position to the extended position.

16. The plunger rod assembly of claim 10, wherein the non-helical radial extension comprises a rigid protrusion.

17. The plunger rod assembly of claim 10, wherein, when the plunger rod is in the collapsed position, twisting the outer member relative to the inner member in a first direction causes the radial extension to initially pass through the helical portion of the track, and wherein continued twisting of the outer member relative to the inner member in the first direction moves the radial extension into the circumferential portion of the track.

18. The plunger rod assembly of claim 17, wherein a length of the helical portion of the track is greater than a length of the circumferential portion of the track.

* * * * *